US012594024B2

(12) United States Patent
Yang et al.

(10) Patent No.: US 12,594,024 B2
(45) Date of Patent: Apr. 7, 2026

(54) METHOD FOR PREDICTING SURVIVAL OF NON SMALL CELL LUNG CANCER PATIENTS WITH BRAIN METASTASIS

(71) Applicant: THE CATHOLIC UNIVERSITY OF KOREA INDUSTRY-ACADEMIC COOPERATION FOUNDATION, Seoul (KR)

(72) Inventors: Seung Ho Yang, Seoul (KR); Young Il Kim, Suwon-si (KR); Hyun Ho Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 18/620,652

(22) Filed: Mar. 28, 2024

(65) Prior Publication Data

US 2024/0415448 A1     Dec. 19, 2024

(30) Foreign Application Priority Data

Jun. 19, 2023    (KR) ........................ 10-2023-0078451

(51) Int. Cl.
A61B 5/00        (2006.01)
A61B 5/055        (2006.01)

(52) U.S. Cl.
CPC ............ A61B 5/4519 (2013.01); A61B 5/055 (2013.01)

(58) Field of Classification Search
CPC ..... A61B 5/4519; A61B 5/055; A61B 5/0042; A61B 5/0803; A61B 5/7275; G06T 7/60; G06T 2207/10088; G06T 2207/30016
See application file for complete search history.

(56) References Cited

FOREIGN PATENT DOCUMENTS

KR    10-2017-0116342    10/2017
KR    10-2023-0060686    5/2023

OTHER PUBLICATIONS

Cinkir, Havva. (2020). The Prognostic Effects of Temporal Muscle Thickness and Inflammatory-Nutritional Parameters on Survival in Lung Cancer Patients with Brain Metastasis. Turkish Journal of Oncology. 10.5505/tjo.2019.2030. (Year: 2020).*
Matsumura, S., Kato, T., Kujime, Y. et al. Pre-treatment metastatic growth rate is associated with clinical outcome in patients with metastatic renal cell carcinoma treated with nivolumab. BMC Urol 23, 107 (2023). https://doi.org/10.1186/s12894-023-01248-z (Year: 2023).*
Association between temporal muscle thickness and clinical outcomes in patients with newly diagnosed glioblastoma Geon An, Stephen Ahn, Jae-Sung Park, Sin-Soo Jeun, Yong-Kil Hong doi: https://doi.org/10.1101/2020.07.02.20145342 (Year: 2020).*

(Continued)

*Primary Examiner* — Pascal M Bui Pho
*Assistant Examiner* — Nicholas A Robinson
(74) *Attorney, Agent, or Firm* — NORTON ROSE FULBRIGHT US LLP

(57)        ABSTRACT
The present invention relates to a method for predicting survival of non-small cell lung cancer patients with brain metastasis. More specifically, it proposes a method that is useful for predicting the survival of the patients by comparing TMTrg of the patients with cut off value for predicting long term survival.

3 Claims, 2 Drawing Sheets

(56) References Cited

OTHER PUBLICATIONS

Furtner et al., "Survival prediction using temporal muscle thickness measurements on cranial magnetic resonance images in patients with newly diagnosed brain metastases" *Eur Radiol* (2017) 27, pp. 3167-3173.

Ilic et al., "Combined Assessment of Preoperative Frailty and Sarcopenia Allows the Prediction of Overall Survival in Patients with Lung Cancer (NSCLC) and Surgically Treated Brain Metastasis", *Cancers*, 2021, 13, 3353, pp. 1-10.

Kim et al., "Association between Temporal Muscle Thickness and Overall Survival in Non-Small Cell Lung Cancer Patients with Brain Metastasis", *Current Oncology*, 2022, 29, pp. 6463-6471.

Kim et al., "The Effect of Temporal muscle thickness (TMT) Changes on Overall Survival in Non-small cell lung cancer (NSCLC) patients with brain Metastasis" *Department of Neurosurgery, St. Vincent's Hospital, College of Medicine, The Catholic University of Korea*, Poster, Jun. 15, 2023.

Oh et al., "The Effect of Temporal muscle thickness (TMT) Changes on Overall Survival in Non-small cell lung cancer (NSCLC) patients with brain Metastasis" *Department of Neurosurgery, St. Vincent's Hospital, College of Medicine, The Catholic University of Korea*, Presentation, 41st Spring Conference of the Korean Neurosurgical Society, Mar. 31, 2023, 18 pages.

* cited by examiner

METHOD FOR PREDICTING SURVIVAL OF NON SMALL CELL LUNG CANCER PATIENTS WITH BRAIN METASTASIS

STATEMENTS OF GOVERNMENT SUPPORT

This research was supported by a grant of Korean ARPA-H Project through the Korea Health Industry Development Institute (KHIDI), funded by the Ministry of Health & Welfare, Republic of Korea (Grant number: RS-2025-25454431). This research was supported by a grant of the Korea Health Industry Development Institute (KHIDI), funded by the Ministry of Health & Welfare, Republic of Korea (Grant number: RS-2025-25459885).

CROSS-REFERENCE TO RELATED APPLICATION

This application claims priority to and the benefit of Korean Patent Application No. 10-2023-0078451, filed on Jun. 19, 2023, the disclosure of which is incorporated herein by reference in its entirety.

FIELD OF THE DISCLOSURE

The present invention relates to a method for predicting survival of non-small cell lung cancer patients with brain metastasis by comparing the calculated TMTrg (temporal muscle thickness reduction gradient) of the patients to the cut-off value of TMTrg.

DESCRIPTION OF RELATED ART

Non-small cell lung cancer is a malignant tumor that occurs in the lung. Non-small cell lung cancer is classified into non-small cell lung cancer and small cell lung cancer. Non-small cell lung cancer accounts for approximately 85% to 90% of lung cancers, and non-small cell lung cancer encompasses various types of cancer which is composed of non-small cell components.

Brain metastasis means that cancer spreads from the primary tumor to another area. Lung cancer has the characteristic of easily spreading to other organs, and the brain is one of the common sites of metastasis. When lung cancer spreads to the brain, it is called the brain metastasis of lung cancer.

Brain metastases are mainly caused by the progression of lung cancer or the movement of cancer cells through blood or lymphatic vessels. Brain metastases can cause a variety of symptoms, and common symptoms include headaches, dry mouth, back and leg pain, balance problems, cognitive decline and the like. If brain metastasis occurs, the patient's prognosis worsens, and treatment may become difficult.

As the related art, according to Patent Document 1 (Korean Patent Application Laid-Open No. 10-2023-0060686), disclosed is a method for predicting the survival of non-small cell lung cancer patients by utilizing clinical data and PET images based on artificial intelligence, and according to Patent Document 2 (Korean Patent Application Laid-Open No. 10-2017-0116342), disclosed is a method for predicting the survival of patients with lung cancer by utilizing a lung cancer prognostic biomarker using a single-nucleotide polymorphism in the intron of the EGFR gene. Among studies on the survival of lung cancer patients with brain metastasis, several studies have found a correlation between temporal muscle thickness at the time of diagnosis of brain metastasis and survival. However, there has so far been no attempt to predict their survival through changes of temporal muscle thickness.

Accordingly, the inventors of the present invention defined a new formula for evaluating changes in temporal muscle thickness in order to predict the survival of non-small cell lung cancer patients with brain metastasis, and completed the present invention by confirming that this value had a statistically significant correlation with survival prognosis.

SUMMARY

An object of the present invention is to provide a method for predicting the survival of non-small cell lung cancer patients with brain metastasis by utilizing the TMTrg (temporal muscle thickness reduction gradient).

In order to achieve the above object, the present invention provides a method for predicting survival of non-small cell lung cancer patients with brain metastasis, comprising steps of (a) calculating the TMTrg (temporal muscle thickness reduction gradient) from the patients as calculated by Formula 1 below; and (b) predicting survival of the patients by comparing the calculated TMTrg to the cut-off value of TMTrg:

$$\text{TMT reduction gradient (TMTrg)} = \frac{\text{(Final TMT (mm)} - \text{Initial TMT (mm))}}{\text{Follow-up period (Months)}} \qquad \text{[Formula 1]}$$

The method for predicting survival of non-small cell lung cancer patients with brain metastasis according to the present invention can be advantageously useful in future research on survival prediction of non-small cell lung cancer patients with brain metastasis.

Figure 1:
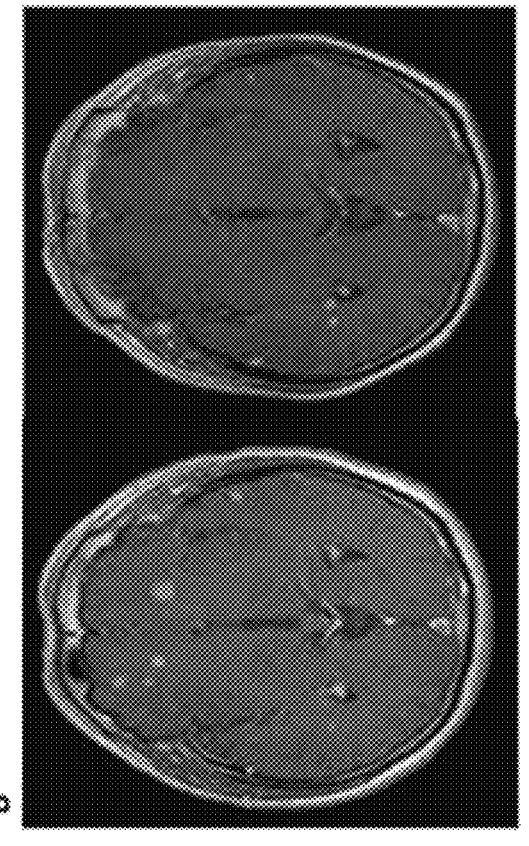
FIG. 1 shows the representative examples of TMTrg calculated in the brain MRI. (A) is an MRI of a lung cancer patient (55-year-old female) with multiple brain metastases with an overall survival time of 67 months, wherein the average temporal muscle thickness of left and right on the initial and final T1 CE axial brain MRI are 7.2 mm and 4.2 mm, respectively. In conclusion, the TMTrg in FIG. 1A is calculated as −0.04 (4.2−7.2/67).
Figure 1:
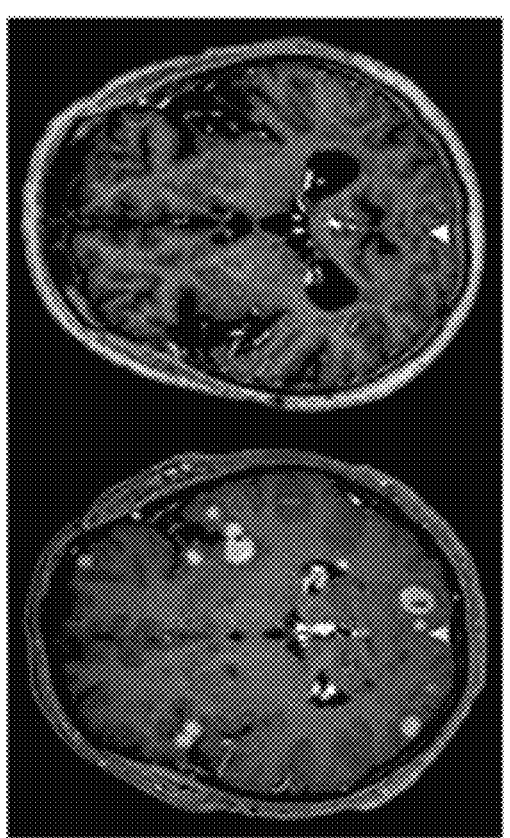

(B) is an MRI of a lung cancer patient (67-year-old male) with multiple brain metastases with an overall survival time of 3 months, wherein the average temporal muscle thickness of left and right on the initial and final T1 CE axial brain MRI are 9.3 mm and 7.6 mm, respectively. In conclusion, the TMTrg in FIG. 1B is calculated −0.56 ((7.6−9.3)/3).

Figure 2:
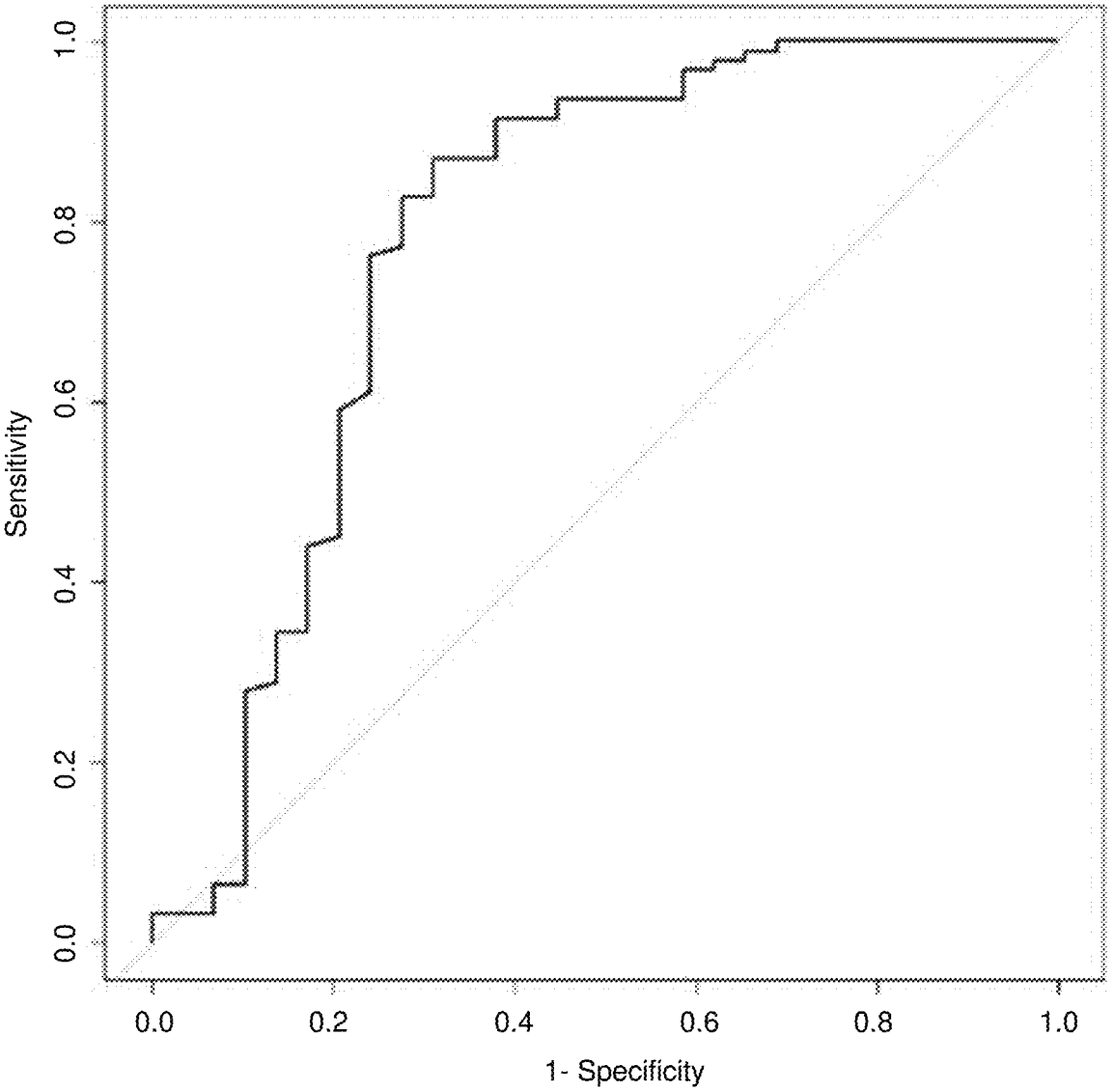

FIG. 2 shows a TMTrg cutoff value for the survival of 6 months or more by using ROC analysis.

DETAILED DESCRIPTION OF THE INVENTION

Hereinafter, the present invention will be described in detail.

The terms used in the present invention are general terms that are currently widely used as much as possible while considering the function of the present invention, but these may vary depending on the intention of a person skilled in the art working in this technical field or the emergence of new technology. Additionally, in certain cases, there are terms that are arbitrarily selected, and in this case, the meaning will be described in detail in the description part of the relevant exemplary embodiments. Therefore, the terms used in the present invention should be defined based on the meanings of the terms and the overall content of the present invention, rather than simply the names of the terms.

The definitions of terms used in the present invention are as follows.

"Prognosis" refers to the course of a neoplastic disease such as lung cancer, including the likelihood or progression of lung cancer-related death, including onset, recurrence, metastatic spread and drug resistance, and whether it is cured. For the purposes of the present invention, prognosis specifically refers the survival prognosis after onset of brain metastasis in patients with non-small cell lung cancer.

"Prediction" is associated with the likelihood of survival or whether patients will survive after the patients are treated by, for example, a particular therapeutic agent, and/or surgical removal of the primary tumor, and/or chemotherapy for a certain period of time without the recurrence of cancer by determining whether patients are likely to develop lung cancer and responding favorably or unfavorably to treatment, such as chemotherapy or radiation therapy. The prediction method of the present invention may determine whether the long-term survival of the patients are possible after the treatment prescription.

"Treatment" means an approach to obtain a beneficial or desirable clinical outcome. For the purposes of the present invention, beneficial or desirable clinical outcomes include the alleviation of symptoms, the reduction of the scope of disease, the stabilization of a disease state, a delay or reduction in the rate of disease progression, the amelioration or palliation and alleviation of a disease state, whether it is detected and the like, but the present invention is not limited thereto. "Treatment" may also mean increasing survival compared to survival expected without treatment. Treatment refers to both of therapeutic and preventive treatment methods. The treatments include treatments that are required for disorders that have already occurred as well as disorders that are being prevented.

Hereinafter, the present invention will be described in detail.

The present invention provides a method for predicting survival of non-small cell lung cancer patients with brain metastasis, comprising the steps of (a) calculating the TMTrg (temporal muscle thickness reduction gradient) from the patients as calculated by Formula 1 below; and (b) predicting survival of the patients by comparing the calculated TMTrg to the cut-off value of TMTrg:

$$\text{TMT reduction gradient (TMTrg)} = \frac{\text{(Final TMT (mm)} - \text{Initial TMT (mm))}}{\text{Follow-up period (Months)}} \quad \text{[Formula 1]}$$

The non-small cell lung cancer refers to a malignant tumor that occurs in the lung, which accounts for more than 80% of lung cancer, and examples thereof include squamous cell carcinoma that occurs in the center of the lung, adenocarcinoma that occurs at the edge of the lung, large cell cancer and the like. Non-small cell lung cancer generally progresses slower than small cell lung cancer, and it has the characteristic of gradually spreading throughout the body through nearby lymph nodes.

The cut-off value of TMTrg for predicting the patients' long term survival may be −0.185.

According to an embodiment of the present invention, the cut-off value was derived through ROC curve with TMTrg of NSCLC patients diagnosed with brain metastasis at St. Vincent's Hospital from 2009 to 2018.

The Final TMT in Formula 1 may be the TMT measured at the survival prediction point when calculating TMTrg in the patients, and is the TMT measured at the last follow-up point before death when deriving the cut-off value of TMTrg.

The Initial TMT in Formula 1 may be the TMT measured at the point of the patients' brain metastasis.

The temporal muscle thickness (TMT) may be measured in MRI of the patients, but the present invention is not limited thereto.

The Follow-up period in Formula 1 may be the interval between initial TMT measurement time point and final TMT measurement time point.

The method for predicting survival of non-small cell lung cancer patients with brain metastasis may further include the steps of predicting that the survival period is 6 months or more when the TMTrg is −0.185 or more, and predicting that the survival period is less than 6 months when the TMTrg is less than −0.185.

If TMT measurement through MRI is conducted within 6 months after the first diagnosis of brain metastasis, the TMTrg at that time can be calculated and compared to the TMTrg cut-off value −−0.185. This comparison can be used as a method to predict the possibility that the patients will survive less than 6 months or more than 6 months.

In addition, the patients are not limited by clinical characteristics such as gender, pathological diagnosis, performance score, the imaging characteristics of brain metastasis and the local treatment of brain metastases.

Hereinafter, the present invention will be described in more detail through examples. These examples are for illustrating the present invention in more detail, and the scope of the present invention is not limited to these examples.

Example 1: Experimental Materials and Methods

1-1. Research Subject

Electronic medical records of NSCLC patients who were diagnosed with brain metastasis at St. Vincent's Hospital from 2009 to 2018 were reviewed. Cases of (1) having pathologically confirmed non-small cell lung cancer at the primary site or other metastatic sites, and (2) having brain metastasis confirmed by magnetic resonance imaging (MRI) by a neuroradiologist or pathologically confirmed by a neuropathologist were included, and cases were excluded if (1) baseline clinical variables, including temporal muscle thickness, were not accessible, (2) survival data were not available, and (3) there was an underlying brain tumor before the diagnosis of brain metastasis.

1-2. Measurement of Temporal Muscle Thickness

TMT was measured by using axial 1 mm slice contrast-enhanced T1-weighted MRI which was performed at the time of initial diagnosis of brain metastasis. The axial MRI plane was placed to be parallel to the anterior commissure-posterior commissure line. The perpendicular line with respect to the long axis of the temporal muscle was set by using the Sylvian fissure (anterior-caudal direction) and orbital roof (cranio-caudal direction of the temporal muscle) as anatomical landmarks.

1-3. Clinical Variables

Clinical variables included gender, age, pathological diagnosis, treatment method that the patients received after the diagnosis of brain metastasis, imaging findings of brain metastasis, performance status upon the diagnosis of brain metastasis, survival status and/or the date of death. After brain metastasis were diagnosed, local treatment included radiotherapy, radiosurgery or surgical resection. Through comprehensive discussion, the most appropriate treatment method for the patient was selected, by taking into account the characteristics of brain metastasis and the patient's condition. Performance status was estimated according to the Eastern Cooperative Oncology Group (ECOG) scale.

The presence of EGFR (Epidermal Growth Factor Receptor) gene mutations was assessed by polymerase chain reaction. The presence of ALK (anaplastic lymphoma kinase) gene mutations was assessed by immunohistochemical staining. Survival status and/or death date were collected through the Korean Central Cancer Registry database.

1-4. Statistical Analysis

The overall survival was calculated by using the period from the date of brain metastasis diagnosis to the date of death. Patients who were alive on Dec. 31, 2021 were censored.

Example 2: Experimental Results

2-1. Patient Analysis

The baseline characteristics of the above patients at the time of brain metastasis diagnosis are shown in Table 1. The average age of the patients who were subject to research was 64.2 years old, and among these patients, 166 patients had adenocarcinoma, 30 patients had squamous cell carcinoma, 3 patients had large cell carcinoma, and 5 patients had sarcomatoid carcinoma. Among the above patients, 64 patients had 1 brain metastasis, 67 patients had 2 to 4 brain metastases, and 90 patients had 5 or more brain metastases. In addition, there were 104 patients with extracranial metastases.

As a result of the Eastern Cooperative Oncology Group (ECOG) measurement, which is a scale that evaluates the patient's daily life movement ability, physical activity ability and fatigue, there were 127 patients with an ECOG of 0 to 1, and 94 patients with an ECOG of 2 or more.

Among the above patients, 154 patients received radiotherapy, 22 patients received radiosurgery, and 18 patients received surgical resection.

As a result of testing EGFR mutations (Epidermal Growth Factor Receptor mutation) to measure genetic mutations associated with lung cancer, 89 patients had EGFR mutations, 89 did not, and 43 patients had unknown metastasis.

As a result of testing for ALK mutations (Anaplastic Lymphoma Kinase mutation) to measure genetic mutations associated with non-small cell lung cancer, 3 patients had ALK mutation, 110 patients did not, and 108 patients had unknown metastasis.

TABLE 1

| Variates | |
| --- | --- |
| Male, n (%) | 133(60.2) |
| Age, Year, n (range) | 64.2(33-90) |
| TMT, mm (range) | |
| Male | 7.7(2.4-14.8) |
| Female | 7.0(2.4-11.7) |
| Pathological diagnosis, n (%) | |
| Adenocarcinoma | 166(75.1) |
| Squamous cell carcinoma | 30(13.6) |
| Large cell carcinoma | 3(1.3) |
| Sarcomatoid carcinoma | 5(2.3) |
| Others | 17(7.6) |
| Number of brain metastases, n (%) | |
| 1 | 64(29.0) |
| 2-4 | 67(30.3) |
| <5 | 90(40.7) |
| Extracranial metastases, n (%) | 104(47.1) |

TABLE 1-continued

| ECOG, n (%) | |
| --- | --- |
| 0-1 | 127(57.5) |
| >2 | 94(42.5) |
| Radiotherapy, n (%) | 154(70.0) |
| Radiosurgery, n (%) | 22(10.0) |
| Surgical resection, n (%) | 18(8.1) |
| EGFR mutation, n (%) | |
| Cases where there is mutation | 89(40.3) |
| Cases where there is no mutation | 89(40.3) |
| Unknown cases | 43(19.4) |
| ALK mutation, n (%) | |
| Cases where there is mutation | 3(1.4) |
| Cases where there is no mutation | 110(49.8) |
| Unknown cases | 108(48.9) |

2-2. Analysis of TMTrg Values and Derivation of Cutoff Value

Cox regression analysis and Cox proportional-hazard model were used to analyze the correlation between the temporal muscle thickness reduction gradient (TMTrg) values and overall survival.

In addition, the ROC (Receiver Operating Characteristic) curve was used to derive the cutoff value of the temporal muscle thickness reduction gradient (TMTrg) in patients who survived for more than 6 months (FIG. 2).

2-3. ROC Analysis Experiment

ROC analysis was performed to determine whether TMTrg showed a significant difference based on 6 months survival. The analysis was performed by coding the patient's survival period of 6 months or more as 1, and if it was less than 6 months, it was coded as 0.

As a result, the area under the curve (AUC) value was 0.7811 (95% CI: 0.6603-0.9018), and the cutoff value was confirmed to be −0.185.

2-4. Univariate Analysis and Multivariate Analysis

Univariate and multivariate analyses were performed on the patients' variables in Cox proportional hazards regression analysis (Table 2). If the hazard ratio was greater than 1, the factor was considered to shorten survival time, if it was less than 1, the factor was considered to increase survival time, and if it was 1, the factor was considered to have no effect on survival time.

Age, initial TMT, TMTrg and ECOG were analyzed as continuous variables, and gender (female 0, male 1), EGFR (wild type: 0, mutation: 1) and ALK (wild type: 0, mutation: 1) were analyzed as categories.

In the case of gender, the death hazard ratio (HR) of male patients was quantified based on the death hazard ratio (HR) of female patients.

As a result of the analysis, the risk of death for men was 1.43, the risk of death for EGFR was 0.61 times higher for the mutation type than for the wild type, and the risk of death for ALK was 0.30 times higher for the mutation type than the wild type.

In addition, as a result of univariate and multivariate analyses of TMTrg, the hazard ratios were confirmed to be 0.17 and 0.08, respectively, which confirmed that as the gradient of TMTrg was gentler, the patient's survival period became longer.

TABLE 2

| Characteristics | Number | Univariate | | | | Multivariate | | | |
|---|---|---|---|---|---|---|---|---|---|
| | | HR | 95% CI | | p-value | HR | 95% CI | | p-value |
| Gender | 221 | | | | | | | | |
| Female | | — | — | | | — | — | | |
| Male | | 1.43 | 1.08 | 1.88 | 0.012 | 0.41 | 0.2 | 0.82 | 0.012 |
| Age | 221 | 1.03 | 1.02 | 1.05 | <0.001 | 1.04 | 1.01 | 1.07 | 0.003 |
| Initial TMT | 221 | 0.9 | 0.84 | 0.97 | 0.004 | | | | |
| TMTrg | 122 | 0.17 | 0.1 | 0.26 | <0.001 | 0.08 | 0.03 | 0.21 | <0.001 |
| EGFR | 179 | 0.61 | 0.45 | 0.82 | 0.001 | 0.30 | 0.14 | 0.65 | 0.002 |
| ALK | 113 | 0.30 | 0.07 | 1.21 | 0.090 | 0.27 | 0.06 | 1.26 | 0.095 |
| ECOG | 221 | 1.21 | 1.00 | 1.47 | 0.049 | | | | |

HR = Hazard Ratio,
CI = Confidence Interval

The terms used in the present invention should not be construed as being limited to their common or dictionary meanings, but should be interpreted with meanings and concepts that are consistent with the technical idea of the present invention.

REFERENCES

Patent Documents:
1. Korean Patent Application Laid-Open No. 10-2023-0060686 (May 28, 2023)
2. Korean Patent Application Laid-Open No. 10-2017-0116342 (Oct. 19, 2017)

Non-Patent Documents:
1. Young II Kim et al, Association between Temporal Muscle Thickness and Overall Survival in Non-Small Cell Lung Cancer Patients with Brain Metastasis, Curr. Oncol. 2022, 29 (9), 6463-6471
2. Inja Ilic et al, Combined Assessment of Preoperative Frailty and Sarcopenia Allows the Prediction of Overall Survival in Patients with Lung Cancer (NSCLC) and Surgically Treated Brain Metastasis. Cancers 2021, 13, 3353
3. Julia Furtner et al, Survival prediction using temporal muscle thickness measurements on cranial magnetic resonance images in patients with newly diagnosed brain metastases. Eur Radiol. 2017; 27 (8): 3167-3173

The invention claimed is:

1. A method of treating a patient diagnosed with a non-small cell lung cancer with brain metastasis, the method comprising:
   (a) calculating a temporal muscle thickness reduction gradient (TMTrg) from the patient as calculated by:

TMTrg=(Final temporal muscle thickness (TMT)–Initial TMT)/Follow-up period, wherein,
   the Final TMT is a TMT measured at a survival prediction point and is measured in millimeters (mm);
   the Initial TMT is a TMT measured at initial diagnosis of the patients' brain metastasis and measured in mm; and
   the Follow-up period is an interval between Initial TMT measurement time point and Final TMT measurement time point and measured in months; and
   (b) treating the patient with surgery, chemotherapy, radiation, or administering a therapeutic agent when the calculated TMTrg is –0.185 or more and less than 0.

2. The method of claim 1, further comprising treating the patient with palliation of the non-small cell lung cancer with brain metastasis when the patient's calculated TMTrg is not –0.185 or more and less than 0.

3. The method of claim 1, wherein calculating the Final TMT and the Initial TMT is performed with magnetic resonance imaging data.

* * * * *